(12) United States Patent
Armstrong et al.

(10) Patent No.: US 7,029,886 B1
(45) Date of Patent: Apr. 18, 2006

(54) ENZYMATIC SUBSTRATE, SYNTHESIS METHOD AND USES

(75) Inventors: Lyle Armstrong, Northumberland (GB); Arthur James, Tyne and Wear (GB)

(73) Assignee: Bio Merieux, Marcy l'Etoile (FR)

( * ) Notice: Subject to any disclaimer, the term of this patent is extended or adjusted under 35 U.S.C. 154(b) by 373 days.

(21) Appl. No.: 10/111,674

(22) PCT Filed: Oct. 25, 2000

(86) PCT No.: PCT/FR00/02971

§ 371 (c)(1),
(2), (4) Date: Jul. 26, 2002

(87) PCT Pub. No.: WO01/30794

PCT Pub. Date: May 3, 2001

(30) Foreign Application Priority Data

Oct. 28, 1999 (FR) .................................. 99 13756

(51) Int. Cl.
*C12N 9/00* (2006.01)
(52) U.S. Cl. ..................................................... 435/183
(58) Field of Classification Search .................. 435/34, 435/183
See application file for complete search history.

(56) References Cited

U.S. PATENT DOCUMENTS 4,667,032 A * 5/1987 Lau et al. ...................... 544/35
5,358,854 A 10/1994 Ferguson
5,364,767 A 11/1994 Flowers et al.

FOREIGN PATENT DOCUMENTS

| EP | 0 656 421 A1 | 6/1995 |
| JP | A 1-19088 | 1/1989 |
| JP | A 1-42497 | 2/1989 |
| WO | WO 97/41138 | 11/1997 |
| WO | WO 99/09207 | 2/1999 |

OTHER PUBLICATIONS

Afanas'eva et al. Reactions of benzo[a]phenoxazin-9-one with arylsufinic acids. Zhurnal Obschei Khimii. 1964, vol. 34. No. 12, pp. 3893-3898.*
Dudley et al. Potential naphthoquinone antimalarials. 2-Acylhydrazino-1,4-naphthoquinones and related compounds. Journal of Organic Chemistry, 1969. vol. 34, No. 9, pp. 2750-2755.*
Rehberg et al. Synthesis of 5,7-dihydrobenzo[a]phenazin-5-one derivatives. Journal of Heterocyclic Chemistry. 1995. vol. 32. No. 5, pp. 1643-1644.*
Agrawal et al. Synthesis of benzo[a][1,4]benzothiazino[3,2-c]phenothiazines and 5H-benzo[a]phenothizin-5-ones. Journal of Chemical and Engineering Data. 1975, vol. 20. No. 2, pp. 199-201.*
Tokutake et al., "Glycosides Having Chromophores as Substrates for Sensitive Enzyme Analysis. I. Synthesis of Phenolindophenyl-beta-D-glucopyranosides as substrated for beta-glucosidase", Chem. Pharm. Bull. 1990, vol. 38, No. 1, pp. 13-18.
H. Kodaka et al., "Evaluation of New Medium with Chromogenic Substrates for Members of the Family Enterobacteriaceae in Urine Samples", Journal of Clinical Microbiology, Jan. 1995, pp. 199-201.
M. Manafi, "Culture Media Containing Fluorogenic and Chromogenic Substrates", De Ware(n)-Chemicus 28 (1998), pp. 12-17.
M. Manafi et al., "Fluorogenic and Chromogenic Substrates Used in Bacterial Diagnostics", Microbiological Reviews< Sep. 1991, pp. 335-348.
Y. Lasne, "Immunodosages Avec Marqueurs Enzymatiques", Marqueurs Enzymatiques, Chapter 7, pp. 109-132.
G. H. Keller, "Non-Radioactive Labeling Procedures", DNA Probes pp. 173-376.
J. Sambrook et al., "Molecular Cloning", vol. 1, Cold Spring Harbor Laboratory Press, 1989, pp. 1.85-1.110.
J. Sambrook et al., "Molecular Cloning" vol. 3, Cold Spring Harbor Laboratory Press, 1989, pp. 16.56-16.67.

* cited by examiner

*Primary Examiner*—Christopher R Tate
*Assistant Examiner*—Marcela M Cordero Garcia
(74) *Attorney, Agent, or Firm*—Oliff & Berridge, PLC

(57) ABSTRACT

The invention concerns novel enzymatic substrates of general formula (I) wherein: X represents a nitrogen atom or a carbon atom substituted with a phenyl group, said phenyl group being optionally substituted in meta or para position: Y and Z represent a hydrogen atom when X represents a carbon atom or Y and Z represent together an ether, thioether or amine bond optionally substituted with an alkyl or aryl group; $R_1$ and $R_2$ independently represent each H, Cl, F, I, Br and can be identical or different or $R_1$ and $R_2$ together represent a substituted or non-substituted fused benzene ring, $R_3$ and $R_4$ independently represent each H, Cl, F, I, Br and can be identical or different; R represents a group such that the O—R bond is capable of being hydrolysed by an enzyme. The invention also concerns a method for synthesizing said substrates, a composition, a kit and a method for detecting at least one micro-organism using said enzymatic substrate.

50 Claims, No Drawings

ENZYMATIC SUBSTRATE, SYNTHESIS METHOD AND USES

The present invention relates to a novel family of enzymatic substrates and to uses thereof, in particular for detecting microorganisms.

The detection and identification of bacteria is very important in medicine or in the food industry, since it is known that the organisms can not only prove to be pathogenic agents, but can also reveal certain types of contamination.

Recent methods developed with this aim exploit the use of colored or fluorescent compounds, and the uses of these compounds have been described, for example, in the reviews by M. Manafi et al., Microbiological Reviews, 55(3), pp. 335–348, 1991 or, more recently, M. Manafi, De Ware(n) Chemicus, 28, pp. 12–17, 1998.

In general, four groups of compounds can be distinguished:
- fluorescent labels, such as acridine orange, which produce an increase in fluorescence when the label is adsorbed onto the nucleic acids or the proteins of the cells of the microorganisms;
- pH-dependent indicators, such as acridine or 7-hydroxycoumarin, which vary in intensity or in spectrum of color or fluorescence depending on the pH and therefore on the biochemical activity of the microorganisms;
- compounds sensitive to the oxidoreductive nature of the medium, such as methylene blue, which produce a color under the effect of a reducing medium;
- colored or fluorescent substrates of enzymes, which produce, respectively, a color or fluorescence under the effect of hydrolysis in the presence of an enzyme specific for a microorganism or for a group of microorganisms.

Among the latter category, a certain number of substrates have been described, which in particular allow the detection of β-D-glucosidase or β-D-galactosidase, which are important taxinomic markers for microorganisms, and in particular the *Enterobacteriaceae*. Among these substrates, mention may be made of ortho-nitrophenyl derivatives which produce yellow o-nitrophenol after hydrolysis, or fluorescent substrates, such as derivatives of fluorescein or of 4-methylumbelliferone, which produce a fluorescent label. A considerable limitation of these substrates is the phenomenon of diffusion into the culture medium, which makes it more difficult to distinguish between the colony and the background noise.

To solve this problem, other substrates have been used which give an insoluble product after hydrolysis. These substrates remain localized around the bacterial colony without diffusing onto the culture support, which facilitates interpretation of the test.

Among these substrates, indoxyl derivatives (see, for example, Kodaka et al., J. Clin Microbiol., 33, p. 199–201, 1995 or patents U.S. Pat. No. 5,358,854 and U.S. Pat. No. 5,364,767) or esculetin derivatives (see, for example, WO 97/41138) have been developed. For the first, the difficult synthesis greatly increases the cost, limiting the development of industrial applications on a large scale and, in addition, these substrates are sensitive to the medium incubation conditions. For the second, the necessity of adding an iron-based complexing agent to the medium in order to have a colored reaction is a problem for some microorganisms since it may interfere with their metabolism, and in particular that studied.

The present invention describes a novel family of enzymatic substrates which do not have the abovementioned drawbacks since the synthesis of these compounds is simple to carry out, the substrates are insoluble after hydrolysis, they do not diffuse into the medium and they do not require the addition of a complexing agent such as iron or any particular redox conditions.

An object of the present invention is to describe a family of compounds of general formula (I):

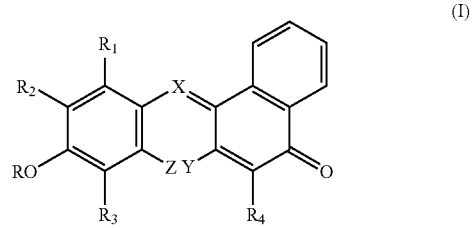

(I)

The enzymes of interest in the present invention are the enzymes whose presence provides information allowing the detection and/or identification and/or quantification of one or more microorganisms or of an analyte, such as a protein, a peptide or a nucleic acid. In particular, the enzyme is from the family of osidases, such as β-glucuronidase, β-galactosidase, 6-phosphogalactohydrolase, α-galactosidase, α-amylase, β-glucosidase, β-glucosidase or the hexosaminidases, for instance N-acetyl-β-glucosaminidase or N-acetyl-α-galactosaminidase, or from the family of esterases, of lipases, of phosphatases, of sulfatases, of DNAases, of peptidases and of proteases. Preferentially, the enzyme is from the family of osidases, such as β-D-glucosidase, β-glucuronidase or β-D-galactosidase, or from the family of sulfatases, phosphatases or esterases.

The group R is chosen as a function of the enzyme to be detected. R is, for example, a residue of the α- or β-sugar type, such as the derivatives of xylose, glucose, galactose, glucuronic acid or glucosamine, or a phosphate, a sulfate, a carboxylate ($R_6COO—$) in which $R_6$ is an alkyl group having from one to 16 carbon atoms, a nucleotide or a peptide. Preferably, the group R is β-D-glucose or β-D-galactose, β-D-glucuronate, a phosphate, a sulfate or an acetate.

When $R_1$ and $R_2$ together represent a fused benzene ring, the following structure (Ia) is intended, which indicates the developed formula for $R_1$ and $R_2$:

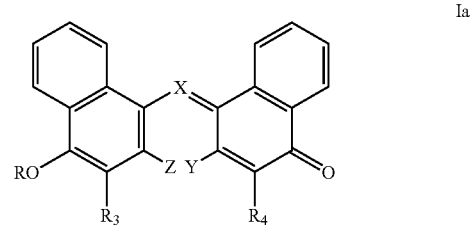

Ia

When Y and Z together represent an ether bond, a bond as represented in general formula (Ib) is intended:

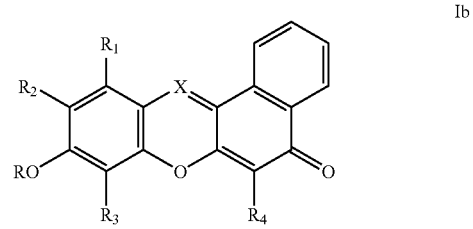

Ib

When Y and Z together represent a thioether bond, a bond as represented in general formula (Ic) is intended:

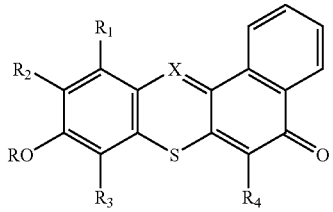

Ic

When Y and Z together represent an amine bond optionally substituted with an aryl or alkyl group, a bond as represented in general formula (Id) is intended:

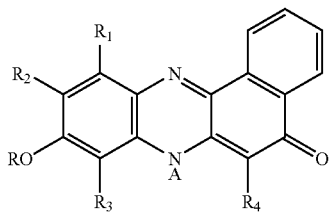

Id in which A represents an aryl or alkyl group.

Particular substrates of general formula (I) are given in general formulae (II), (III), (IVa), (IVb), and (IVc) indicated below:

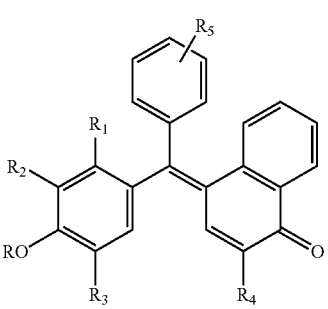

(II)

general formula (II) in which, $R_1$ and $R_2$ each represent, independently of one another, H, Cl, F, I or Br, and may be identical or different, or $R_1$ and $R_2$ together represent a fused benzene ring which may or may not be substituted. Preferentially, $R_1$ and $R_2$ together represent a fused benzene ring which is not substituted, $R_3$ and $R_4$ each represent, independently of one another, H, Cl, F, I or Br, and may be identical or different. Preferentially, $R_3$ and $R_4$ represent H, $R_5$ represents H, $NO_2$, $CF_3$, CN, $OCH_3$, F, I, Cl, Br, $SO_3H$ or $CO_2H$ in the meta or para position. Preferentially, $R_5$ represents H, R represents a group such that the O—R bond can be hydrolyzed by an enzyme. In particular, R represents a residue of the α- or β-sugar type, preferentially β-D-glucose or β-D-galactose, or an acetate or a sulfate.

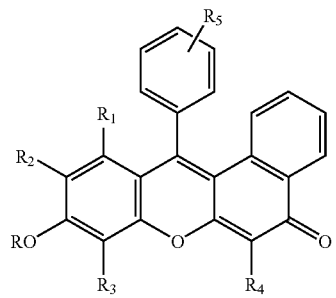

(III)

general formula (III) in which, $R_1$ and $R_2$ each represent, independently of one another, H, Cl, F, I or Br, and may be identical or different, or $R_1$ and $R_2$ together represent a fused benzene ring which may or may not be substituted. Preferentially, $R_1$ and $R_2$ together represent a fused benzene ring which is not substituted, $R_3$ and $R_4$ each represent, independently of one another, H, Cl, F, I or Br, and may be identical or different. Preferentially $R_3$ and $R_4$ represent H, $R_5$ represents H, $NO_2$, $CF_3$, CN, $OCH_3$, F, I, Cl, Br, $CO_2H$ or $SO_3H$ in the meta or para position.

Preferentially, $R_5$ represents H,

R represents a group such that the O—R bond can be hydrolyzed by an enzyme. In particular, R represents a residue of the α- or β-sugar type, preferentially β-D-glucose or β-D-galactose.

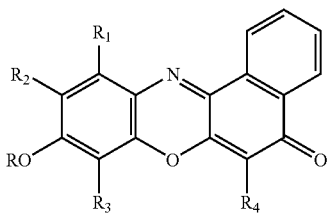

(IVa)

general formula (IVa) in which, $R_1$ and $R_2$ each represent, independently of one another, H, Cl, F, I or Br, and may be identical or different, or $R_1$ and $R_2$ together represent a fused benzene ring which may or may not be substituted. Preferentially, $R_1$ represents H and $R_2$ represents Cl, $R_3$ and $R_4$ each represent, independently of one another, H, Cl, F, I or Br, and may be identical or different. Preferentially $R_3$ and $R_4$ represent H, R represents a group such that the O—R bond can be hydrolyzed by an enzyme. In particular, R represents a residue of the α- or β-sugar type, preferentially β-D-glucose or β-D-galactose or an acetate or a sulfate.

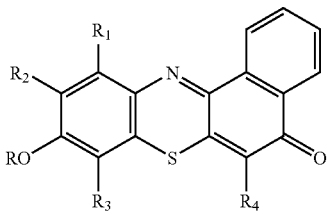

(IVb)

general formula (IVb) in which, $R_1$ and $R_2$ each represent, independently of one another, H, Cl, F, I or Br, and may be identical or different, or $R_1$ and $R_2$ together represent a fused benzene ring which may or may not be substituted. Preferentially, $R_1$ represents H and $R_2$ represents Cl, $R_3$ and $R_4$ each represent, independently of one another, H, Cl, F, I or Br, and may be identical or different. Preferentially, $R_3$ and $R_4$ represent H, R represents a group such that the O—R bond can be hydrolyzed by an enzyme. In particular, R represents a residue of the α- or β-sugar type, preferentially β-D-glucose or β-D-galactose or an acetate or a sulfate.

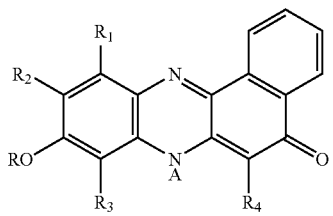

(IVc)

general formula (IVc) in which,

A represents an aryl or alkyl group, $R_1$ and $R_2$ each represent, independently of one another, H, Cl, F, I or Br, and may be identical or different, or $R_1$ and $R_2$ together represent a fused benzene ring which may or may not be substituted. Preferentially, $R_1$ represents H and $R_2$ represents Cl, $R_3$ and $R_4$ each represent, independently of one another, H, Cl, F, I or Br, and may be identical or different. Preferentially, $R_3$ and $R_4$ represent H, R represents a group such that the O—R bond can be hydrolyzed by an enzyme. In particular, R represents a residue of the α- or β-sugar type, preferentially β-D-glucose or β-D-galactose, or an acetate or a sulfate.

The invention also relates to a method for synthesizing the enzymatic substrate of general formula (I), in which an intermediate is prepared, which is of general formula (V)

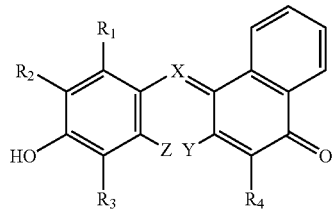

(V)

in which

X represents a nitrogen atom or a carbon atom substituted with a phenyl group, said phenyl group optionally being substituted in the meta or para position, Y and Z represent a hydrogen atom when X represents a carbon atom, or Y and Z together represent an ether, thioether or amine bond optionally substituted with an alkyl or aryl group, $R_1$ and $R_2$ each represent, independently of one another, H, Cl, F, I or Br, and may be identical or different, or $R_1$ and $R_2$ together represent a fused benzene ring which may or may not be substituted, $R_3$ and $R_4$ each represent, independently of one another, H, Cl, F, I or Br, and may be identical or different, and a suitably protected group R is grafted onto the hydroxyl.

In particular, the grafting takes place via a glycosylation, esterification or phosphorylation reaction.

In the case of glycosylation, it is necessary to protect the hydroxyl groups of the sugar, such as for example with an acetyl group. The tetraacetylated derivatives of β-D-glucoside or β-D-galactoside are obtained from the corresponding α-acetobromohexose derivative.

The deprotection of the hydroxyl groups of the sugar is carried out, after grafting, in the presence of an alkaline agent, such as sodium methoxide in methanol for an acetylated derivative. The conditions for glycosylation are chosen by those skilled in the art, and in particular by the action of potassium hydroxide in acetone.

The formation of organic esters, such as acetate, is carried out by reacting, with the derivative of general formula (V), acetic anhydride under cold conditions in pyridine. The formation of an ester of the type $CH_3(CH_2)_nCOOR$ is carried out by reacting an acid chloride derivative in a mixture of solvent of the type pyridine/dimethylformamide, optionally in the presence of a catalyst such as 4-dimethylaminopyridine.

The formation of phosphate is carried out by treating the derivative of general formula (V) in the presence of $POCl_3$, in the presence of pyridine.

The formation of sulfate is carried out by treating the derivative of general formula (V) with chlorosulfonic acid under cold conditions in pyridine. The substrates of the present invention, in the case of phosphates and sulfates, are in the form of a salt, such as potassium or sodium salt.

Advantageously, an intermediate is prepared which corresponds to any one of the following formulae (Va), (Vb) and (Vc):

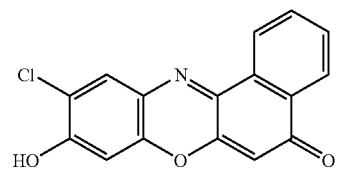

(Va)

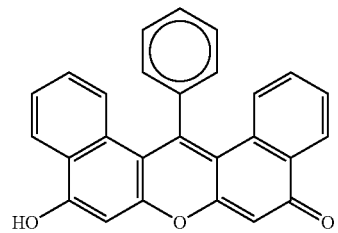

(Vb)

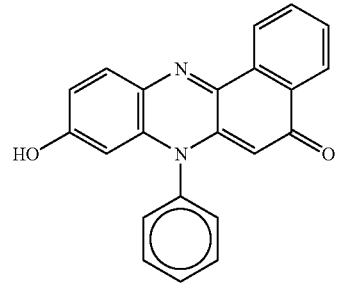

(Vc)

The invention also relates to a composition for detecting and/or identifying and/or quantifying at least one microorganism, comprising at least one enzymatic substrate of general formula (I) and a reaction medium for said microorganism(s).

According to the invention, the term "reaction medium" is intended to mean a medium which allows the development of at least one enzymatic activity of at least one microorganism, such as a culture medium.

The reaction medium is solid, semi-solid or liquid. The term "solid medium" is intended to mean, for example, an agar medium. Agar is the conventional solid medium in microbiology for culturing microorganisms, but it is possible to use gelatin or agarose. A certain number of preparations are available, such as Columbia agar, Trypticase soy agar, MacConkey agar, Sabouraud agar, those described in "Livret technique MILIEU DE CULTURE" [CULTURE MEDIA technical manual] by the Applicant or, more generally, those described in the Handbook of Microbiological Media (CRC Press).

Advantageously, the reaction medium is an agar medium containing between 2 and 40 g/l, preferentially between 9 and 25 g/l, of agar.

The substrates of the present invention can be used in a wide pH range, in particular between pH 5.5 and 10.0, and advantageously between pH 6.0 and 8.5.

The reaction medium may also comprise one or more elements in combination, such as amino acids, peptones, carbohydrates, nucleotides, minerals, vitamins, antibiotics, surfactants, buffers, or phosphate, ammonium, sodium or metal salts. Examples of media are described in the following patents from the Applicant, EP 0656421 or WO 99/09207.

In another aspect of the present invention, the reaction medium comprises at least two enzymatic substrates: a first enzymatic substrate from the family of the invention and at least one other enzymatic substrate from the family of the invention and/or another enzymatic substrate from another substrate family. The enzymatic hydrolysis of the other substrate(s) generates a detectable signal, which is different from the signal generated by the first substrate, such as for example different colored or fluorescent products, so as to allow the demonstration such as the detection and/or the identification and/or the quantification of one or more microorganisms.

By way of example, the following combinations may be envisaged:
  a β-glucuronidase substrate according to the invention and X-β-D-glucoside (X is 5-bromo-4-chloro-3-indolyl) for a medium for urine samples (type CPS ID2, bioMérieuz, Marcy l'Etoile, France);
  a β-galactosidase substrate according to the invention and X-β-D-glucoside for a medium for urine samples (type CHROMagar Orientation (registered trade mark) sold by the company CHROMagar, Paris, France or Oxoid UTI sold by the company OXOID, Hampshire, England);
  a β-glucuronidase substrate according to the invention and X-β-D-galactoside for a medium for *Escherichia coli* and coliforms (type Coli ID, bioMerieux, Marcy l'Etoile, France);

By way of example, use may be made of a hexosaminidase substrate according to the invention for yeasts and the identification of *Candida albicans*.

Substrates according to the present invention may in particular be introduced into the media CPS ID2, SM ID, Albicans ID2, Coli ID and 0157:H7 ID marketed by bioMerieux (Marcy l'Etoile, France) and comprising all or some of their enzymatic substrates, and also into the media comprising esculin, such as Bile Esculin agar, with or without selective agents.

The concentration of the enzymatic substrate in the reaction medium is between 0.02 and 1 g/l, advantageously between 0.03 and 0.30 g/l, and preferentially between 0.04 and 0.10 g/l.

The present invention also extends to a diagnostic kit comprising a composition as defined above and a container for the reaction medium. The term "container" is intended to mean any solid support, such as a bottle, a tube, a dish, a microtitration plate or a consumable product for an automatic machine, for instance API galleries or VITEK cards (registered trade marks, BioMérieux, Marcy l'Etoile, France).

Another aspect of the present invention relates to a method for detecting and/or identifying and/or quantifying at least one microorganism in a specimen, in which the microorganism originating from the specimen is brought into contact with a reaction medium containing an enzymatic substrate of general formula (I), and the colored or fluorescent product formed by the hydrolysis of said enzymatic substrate is detected.

The substrates of general formula (I) have the advantage that they can be used independently of the conditions of the atmosphere for the incubation. The detection can therefore be carried out by incubating the reaction medium containing the enzymatic substrate, and inoculated with at least one microorganism, in a controlled atmosphere, for instance the atmosphere is at least one of aerobic, anaerobic, microaerophilic, or under an atmosphere of $CO_2$, preferably under aerobic or microaerophilic conditions or under an atmosphere of $CO_2$, and preferably aerobic, microaerophilic and under $CO_2$ conditions.

The specimen to be analyzed is a clinical specimen, such as a saliva, blood, urine or stool sample or any other specimen, the analysis of which may aid a clinician in making a diagnosis. The specimen may also be a specimen of a product derived from, or a basic product of, the food and/or pharmaceutical industry, in which it is necessary either to guarantee the absence of pathogenic microorganisms, or to count a contaminating flora or detect specific microorganisms. The specimen may be cultured either directly on a medium containing a substrate of general formula (I), or after a preculturing step, for example in the case of a food sample.

The microorganism(s) which can be identified, detected or quantified in the present invention are bacteria, yeasts and fungi, in particular belonging to the following groups or taxa: *Enterobacteriaceae, Pseudomonadaceae, Nesseriaceae, Vibrionaceae, Pasteurellaceae, Campylobacter, Micrococcaceae, Streptococcaceae, Bacillus, Lactobacillus, Listeria, Corynebacterium, Gardnerella, Nocardia, Candida, Cryptococcus, Aspergillus* and more particularly, *Escherichia coli, E. coli* 0157:H7, *Shigella, Salmonella, Proteeae, Pseudomonas aeruginosa, Neisseria meningitidis, Enterococcus, Staphylococcus aureus, Bacillus cereus, Listeria monocytogenes, Streptococcus pyogenes, Streptococcus agalactiae*, yeasts such as *Candida albicans, Candida glabrata, Candida tropicalis, Cryptococcus neoformans* and *Aspergillus fumigatus*. These microorganisms may be aerobic, aeroanaerobic, microaerophilic or anaerobic.

In another aspect of the present invention, the enzymatic substrates are used in reactions for detecting an analyte, in which an enzymatic activity (in particular alkaline phosphatase or β-galactosidase) is used, such as: the reactions for detecting an antibody or antigen or a nucleic acid, with an ELISA-type format (see, for example, "les immunodosages de la théorie à la pratique" [immunoassays, from theory to practice] coordinated by Y. Barbier, ACOMEN publications, Lyons, pp. 109–133, 1988); in molecular biology techniques for demonstrating a gene of the β-galactosidase type (see, for example, "Molecular cloning: a laboratory manual". 2nd ed., Sambrook, Fritsch, Maniatis, Cold Spring Harbor Laboratory Press, section 16.56 and section 1.85, 1989); for detecting nucleic acids (see, for example, "DNA probes", 2nd edition, G. H. Keller, M. M. Manak, Stockton Press, sections 5 to 9, 1993); or in histochemical, cytochemical or flow cytometry techniques.

The following examples make it possible to illustrate some advantages of the invention without, however, limiting the scope thereof.

EXAMPLE 1

Synthesis of p-naphtholbenzein-β-D-galactoside, PNB-gal product (1)

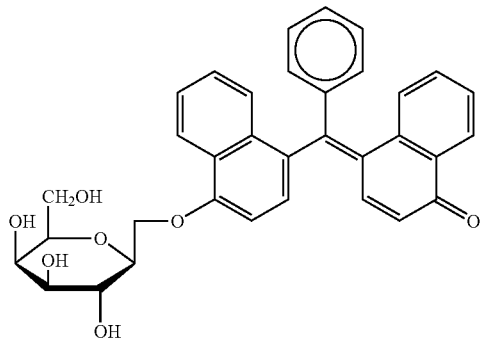

product (1)

p-Naphtholbenzein is obtained from Acros Organics (Geel, Belgium). The other reagents are obtained from Sigma Aldrich Chimie (St Quentin Fallavier, France). The p-naphtholbenzein (1.87 gm, 5 mmol) is dissolved in 20 ml of acetone with vigorous stirring. 5 ml of potassium hydroxide at a concentration of 1.4 mol/liter are added to this solution, followed by 10 ml of acetone. 5 ml of water are then added dropwise so as to generate a dark blue solution. 10 mmol of α-acetobromogalactose (4.1 g) in 10 ml of acetone are added to the solution. In order to maintain the pH at a value greater than 11, 2 ml of a solution of potassium hydroxide at 20 mol/liter are added a first time after 30 minutes of stirring and a second time after 90 minutes of stirring. Alkaline solution is added for a third time after 3.5 hours, followed by the addition of 5 ml of α-acetobromogalactose in acetone at the same concentration as before. After 4.5 hours, alkaline solution is added one last time and the solution is left overnight with stirring.

The acetone is removed under reduced pressure and the residual solution is run into 300 ml of a solution of sodium carbonate at 0.06 mol/l at a temperature of 0° C. with stirring. The chestnut brown precipitate is filtered under vacuum, washed with water and air-dried. The solid is dissolved in 100 ml of dichloromethane and washed thoroughly with a solution of potassium hydroxide at 0° C. in order to remove the excess p-naphtholbenzein. The residual p-naphtholbenzein is removed by stirring on Dowex Marathon resin in 100 ml of water at pH 11, for 2 to 3 hours. This purification is followed by thin-layer chromatography using an ethyl acetate/toluene (3:1) solvent, with developing using aqueous ammonia. The dark yellow solution is dried overnight on anhydrous magnesium sulfate, evaporated under reduced pressure, reconstituted with methanol and then re-evaporated so as to obtain a foam. This foam is dissolved in 50 ml of methanol and the product is deprotected for 5 hours using 20 ml of sodium methoxide in methanol at 0.4 mol/l. The solution is then adjusted to pH 6.5 using an IR120 (H⁺) resin and separated by settling out, and the solvent is removed under reduced pressure. The glycoside formed, p-naphtholbenzein-β-galactosidase, (1.5 g) is in the form of a yellow-chestnut brown powder.

EXAMPLE 2

Synthesis of the acetate derivative of p-naphtholbenzein

The p-naphtholbenzein is dissolved in anhydrous pyridine and then cooled to 0° C., and added to this solution is acetic anhydride (5-fold molar excess) dissolved in pyridine under cold conditions. After 24 hours at ambient temperature, the solution is treated with cold water added dropwise with stirring, in order to decompose the excess acetylating agent. A precipitate of the ester forms, which is removed by filtration under vacuum, washed with acetic acid and recrystallized under hot conditions in acetic acid.

EXAMPLE 3

Synthesis of the sulfate derivative, in the potassium salt form, of p-naphtholbenzein A 1.2 molar excess of chlorosulfonic acid at −15° C. is added, with stirring, to a cold solution of p-naphtholbenzein in anhydrous pyridine. After 1 hour at −15° C. and 30 minutes at ambient temperature, the excess pyridine is evaporated under reduced pressure and the pyridinium salt is decomposed by dissolving in ethanol and treating with a solution of potassium hydroxide in ethanol until a pH of 10 is obtained. The potassium salt is filtered under vacuum and washed with ethanol then diethyl ether.

EXAMPLE 4

Synthesis of 8-chloro-1,2-benzo-resorufin-β-D-glucoside, (CBR-glu) product (2)

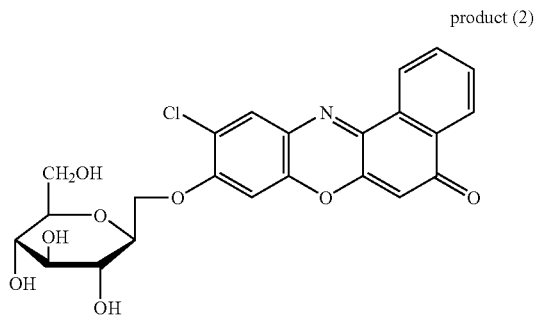

product (2)

6-Nitroso-4-chlororesorcinol (2.94 g, 20 mmol) and 1,3-dihydroxynaphthalene (3.20 g, 20 mmol) are dissolved separately in 1-butanol (30 ml) and mixed. The reaction mixture is heated between 50 and 60° C. using a water bath and sulfuric acid (1.0 g) is added dropwise with stirring for 30 seconds. The solution becomes dark red and crystals rapidly form. After 15 min at 50° C. and 1 hour at ambient temperature, the product is filtered under vacuum and recrystallized from hot 1-butanol to give 2.8 g of brilliant dark red crystals of 8-chloro-1,2-benzoresorufin.

The glucoside derivative (2) is prepared via a Koenigs-Knorr reaction as described previously for the p-naphtholbenzein derivative. The glucoside in a tetraacetylated protected form is isolated by rotary evaporation from dichloromethane and deprotected directly using a catalytic amount of sodium methoxide in anhydrous methanol. The glycoside is in the form of an orangey yellow powder.

EXAMPLE 5

Synthesis of 8-chloro-1,2-benzoresorufin-β-D-galactoside (CBR-gal) product (3)

The method for preparing the β-D-galactoside derivative (3) is identical to that described in example 4, using the β-D-galactoside derivative in the tetraacetylated protected form in place of the glucoside equivalent.

EXAMPLE 6

Synthesis of 3-hydroxy-9-phenyl-1,2:7,8-dibenzo-6-fluorone-β-D-galactoside product (4)

product (4)

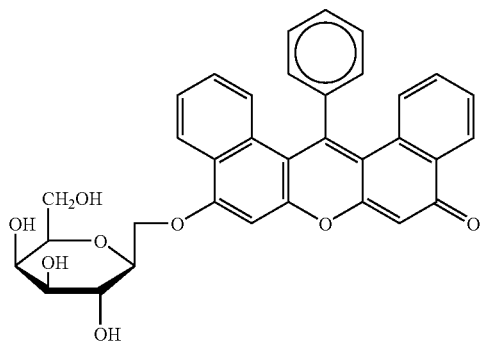

3-Hydroxy-9-phenyl-1,2:7,8-dibenzo-6-fluorone is prepared from 1,3-dihydroxynaphthalene (Aldrich, 14529-7) by condensation under hot conditions with α, α, α-trifluorotoluene (Aldrich, T6370-3) in the presence of a Lewis acid, such as SnCl$_4$ or ZnCl$_2$, in a solvent with a high boiling point, such as chlorobenzene or xylene. After hydrolysis of the Lewis acid and purification of the intermediate compound, the galactoside derivative (4) is prepared as described in example 1.

EXAMPLE 6a

Synthesis of naphthosafranol
(9-hydroxy-7-phenol-5-benzo[a]phenazinone)

product (5)

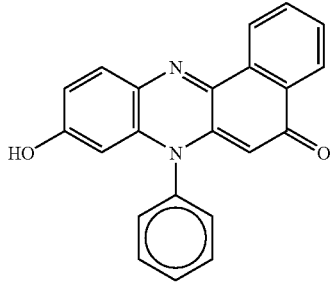

A mixture of 50 g of sulfuric acid and 130 ml of water are added slowly to a solution, maintained at 0° C. and with stirring, of phenol (20 g), sodium nitrite (18 g) and sodium hydroxide (9 g) in 500 ml of water. After reaction for 2 hours, the product is collected and washed with ice-cold water. After recrystallization from water, the p-nitrosphenol product is isolated in pure form (13.4 g).

The p-nitrosophenol thus prepared (12.3 g, 0.1 mol) and also N-phenyl-2-naphthylamine (14.5 g, 0.067 mol, Aldrich, 17,805-5) are dissolved in ethanol (400 ml) and the mixture is cooled to 15° C. Concentrated HCl (15 g) is added to this solution. The temperature rises spontaneously and the isorosindone product (in the form of a hydrochloride salt) is separated by filtration and recrystallized from an ethanol-water (50%—50%) mixture. The recrystallized product may be converted into its free base form by dissolving it firstly in ethanol, then adding ammonium hydroxide and, finally, adding the solution to hot water.

The free base (isorosindone) precipitates in the form of dark chestnut brown crystals upon cooling the solution. Filtration under vacuum produces 15 g of pure product.

The target product (5) is obtained by refluxing the isorosindone in a concentrated solution of KOH in 1-butanol. The product is purified by flash chromatography on silica with ethyl acetate as the eluent.

EXAMPLE 6b

The Galactoside Derivative of Naphthosafranol is Prepared According to the same Protocol as that Described for Example 1

EXAMPLE 7

Use of p-naphtholbenzein-β-D-galactoside (PNB-gal) for Detecting Microorganisms Having β-galactosidase Activity A solid agar medium comprising PNB-gal is prepared as follows: 41 g of Columbia agar are added to 1 liter of distilled water with 100 mg of PNB-gal and 30 mg of IPTG (isopropyl-β-D-thiogalactoside) to facilitate the induction of β-galactosidase activity. The agar is sterilized by autoclaving at 116° C. for 10 min. The medium is cooled slowly to 55° C. before being distributed into 20 ml dishes.

367 different strains, including 303 *Enterobacteriaceae*, are collected from clinical and environmental specimens and identified using the API 20E gallery (BioMérieux, France) as the reference method. The strains are cultured on a Columbia agar medium at 37° C. for 24 hours, and then approximately 10$^8$ organisms/ml (equivalent to a McFarland standard of 0.5) are inoculated for each strain. Using a Denley inoculator, 1 microliter of each suspension is inoculated into the PNB-gal medium prepared above, at 20 strains/dish. All the dishes are incubated at 37° C. for 18 hours. After incubation, the dishes are examined for the presence of a purple colony, in comparison with the growth on the Columbia agar medium. The results are given in table I.

TABLE 1

| Gram-negative species | Number of strains tested for the species | Positive results with the PNB-gal substrate (%) |
|---|---|---|
| *Acinetobacter* spp. | 53 | 0 |
| *Aeromonas caviae* | 7 | 86 |
| *Aeromonas hydrophila* | 3 | 100 |
| *Citrobacter diversus* | 9 | 89 |

TABLE 1-continued

| Gram-negative species | Number of strains tested for the species | Positive results with the PNB-gal substrate (%) |
|---|---|---|
| Citrobacter freundii | 16 | 100 |
| Enterobacter aerogenes | 9 | 100 |
| Enterobacter agglomerans | 1 | 100 |
| Enterobacter cloacae | 21 | 100 |
| Eschericia coli | 41 | 95 |
| Eschericia hermannii | 1 | 100 |
| Hafnia alvei | 10 | 30 |
| Klebsiella oxytoca | 13 | 100 |
| Klebsiella ozaenae | 3 | 67 |
| Klebsiella pneumoniae | 19 | 100 |
| Morganella morganii | 12 | 0 |
| Proteus mirabilis | 16 | 0 |
| Proteus penneri | 1 | 0 |
| Proteus vulgaris | 4 | 0 |
| Providencia alcalifaciens | 3 | 0 |
| Providencia rettgeri | 3 | 0 |
| Providencia stuartii | 10 | 0 |
| Salmonella spp. | 64 | 0 |

TABLE 1-continued

| Gram-negative species | Number of strains tested for the species | Positive results with the PNB-gal substrate (%) |
|---|---|---|
| Serratia odorifera | 1 | 100 |
| Serratia spp. | 14 | 79 |
| Shigella boydii | 1 | 0 |
| Shigella dysenteriae | 2 | 0 |
| Shigella flexneri | 2 | 0 |
| Shigella sonnei | 10 | 100 |
| Vibrio cholerae | 1 | 100 |
| Yersinia enterocolitica | 14 | 7 |
| Yersinia pseudotuberculosis | 3 | 0 |

This table shows that the substrate is very effective as an indicator of β-galactosidase activity. No strain without β-galactosidase activity is detected, which means that there are no false-positives, and the sensitivity on the Enterobacteriaceae strains is 95.1% compared to the API 20E reference method.

EXAMPLE 8

Influence of pH on the revelation of β-D-galactosidase in the presence of p-naphtholbenzein-β-D-galactoside, PNB-gal The medium hereafter, Columbia base at a concentration of 46.37 g/l, isopropyl-β-D-thiogalactoside (IPTG) at 0.03 g/l, p-naphtholbenzein-β-D-galactoside at 0.1 g/l, was adjusted to various pHs (5.5–6.0–6.5–7.0–7.5–8.0–8.5) at 24° C. after the media had been autoclaved. These various media, distributed into Petri dishes, were inoculated on their own and as three dials using a suspension, at 0.5 McFarland, of well-characterized microorganisms derived from the ATCC or NCTC type collection. The dishes were incubated at 37° C. for 48 hours. The colonies formed were examined visually after 24 and 48 hours of incubation, and the color was noted. The results are given in table II below:

TABLE II

| Strains tested | | TI | pH 5.7 | pH 6.0 | pH 6.5 | pH 7.0 | pH 7.5 | pH 8.0 | pH 8.5 |
|---|---|---|---|---|---|---|---|---|---|
| E. coil | 032 | 24 H | — | — | — | — | — | — | — |
|  |  | 48 H | — | — | — | — | — | — | — |
| E. coli | 115 | 24 H | orange | orange | orange | Orange | orange | orange | chestnut brown |
|  |  | 48 H | orange | orange | orange | Orange | brown | brown | brown |
| S. marcescens | 217 | 24 H | chestnut brown | chestnut brown | chestnut brown | Chestnut brown | chestnut brown | green | green |
|  |  | 48 H | chestnut brown | chestnut brown | chestnut brown | Chestnut brown | green | khaki | khaki |
| E. cloacae | 061 | 24 H | orange | orange | orange | Orange | brown | brown | brown |
|  |  | 48 H | chestnut brown | chestnut brown | chestnut brown | Green | green | khaki | khaki |
| S. typhimurium | 010 | 24 H | — | — | — | — | — | — | — |
|  |  | 48 H | — | — | — | — | — | — | — |
| E. faecalis | 117 | 24 H | — | — | — | — | — | — | — |
|  |  | 48 H | orange | orange | orange | Orange | orange | orange | orange |
| S. agalactiae | 015 | 48 H | — | — | — | — | — | — | — |
|  |  | 48 H | — | — | — | — | — | — | — |
| S. aureus | 008 | 24 H | — | — | — | — | — | — | — |
|  |  | 48 N | — | — | — | — | — | — | — |

— means a lack of coloration, TI represents the time of incubation on the dishes.

Depending on the strains and the duration of incubation, the color of colonies varies as a function of pH. In general, it is more orange to brown at acid pH and green to khaki at alkaline pH. This may make it possible to differentiate various groups of microorganisms, to adjust the color as needed (combination with other enzymatic substrates, pH indicators) or to demonstrate several metabolisms (enzymatic hydrolysis and pH variation), which is an advantage of the PNB-gal substrate.

EXAMPLE 9

Influence of the Reaction Medium on the Revelation of β-D-galactosidase in the Presence of p-naphtholbenzein-β-D-galactoside, PNB-gal The following mixture was added to the Colombia, Trypticase soy (TSA) and Sorbitol MacConkey (SMAC) media:
Isopropyl-β-D-thiogalactoside . . . 0.03 g/l
p-Naphtholbenzein-β-D-galactoside . . . 0.1 g/l After autoclaving, the pH of the media was, at 23° C.: 7.1; 7.1 and 7.2 on the SMAC, TSA and Columbia media, respectively. These various media, distributed into Petri dishes, were inoculated on their own and as three dials using a suspension, at 0.5 McFarland, of well-characterized microorganisms derived from the ATCC or NCTC type collection. The dishes were incubated at 37° C. for 48 hours. The colonies formed were examined visually after 24 and 48 hours of incubation, and the color was noted. The results are given in table III below:

TABLE III

| Strains tested | | TI | SMAC medium | TSA Medium | Columbia medium |
|---|---|---|---|---|---|
| E. coli | 032 | 24 H | — | — | — |
| | | 48 H | — | — | — |
| E. coli | 115 | 24 H | orange | orange | brown-orange |
| | | 48 H | orange | orange | brown |
| E. coli | 206 | 24 H | orange | brown-orange | brown |
| | | 48 H | orange | brown-orange | brown |
| S. marcescens | 217 | 24 H | fuchsia | brown-orange | brown |
| | | 48 H | fuchsia | brown | brown |
| E. cloacae | 061 | 24 H | orange | brown-orange | brown |
| | | 48 H | orange | brown | brown |
| S. typhimurium | 010 | 24 H | — | — | — |
| | | 48 H | — | — | — |
| E. faecalis | 010 | 24H | | — | |
| | | 48 H | | orange | orange |
| S. agalactiae | 015 | 24 H | — | — | — |
| | | 48 H | — | — | — |
| S. aureus | 008 | 24 H | — | — | — |
| | | 48 H | — | — | — |

— signifies a lack of coloration,
TI represents the time of incubation on a dish.

Depending on the strains and the duration of incubation, the color of the colonies varies as a function of the medium. In general, it is orange on the SMAC medium and brown on the Columbia medium, without it being possible to link this difference in color to the pH of the medium. On the SMAC medium, it is possible to differentiate *Serratia marcescens* from the other bacteria, which is not the case on the other two media. In addition, it may be advantageous to be able to adjust the color of the colonies obtained with the p-naphtholbenzein-β-D-galactoside depending on the use of other enzymatic substrates giving other colors (pink or brown for example).

EXAMPLE 10

Influence of the Incubation Atmosphere on the Revelation of β-D-galactosidase in the Presence of p-naphtholbenzein-β-D-galactoside, PNB-gal 5-Bromo-4-chloro-3-indolyl-β-D-galactoside (X-Gal) or p-naphtholbenzein-β-D-galactoside (PNB-Gal) at 0.1 g/l is added to the medium below:

| | |
|---|---|
| Yeast extract | 6 g/l |
| Gelatin peptone | 5 g/l |
| NaCl | 8 g/l |
| Sodium carbonate | 0.1 g/l |
| Isopropyl-β-D-thiogalactoside | 0.03 g/l |
| Agar | 13 g/l |

These various media, distributed into Petri dishes, were inoculated with well-characterized microorganisms derived from the ATCC or NCTC type collection. The dishes were incubated at 37° C. for 48 hours under various atmospheres: aerobiosis (AE), microaerophily (MAP), anaerobiosis (ANA), $CO_2$, via the GENbox system (BioMérieux, France) for controlling the atmosphere. The colonies formed were examined visually after incubating for 24 to 48 hours, and the intensity of coloration was noted. The results are given in table IV below:

TABLE IV

| | | | X-Gal | | | | PNB-Gal | | | |
|---|---|---|---|---|---|---|---|---|---|---|
| Strains | | TI | AE Test 1 | MAP Test 2 | ANA Test 3 | $CO_2$ Test 4 | AE Test 5 | MAP Test 6 | ANA Test 7 | $CO_2$ Test 8 |
| E. coli | 115 | 24 H | 3* | 2 | — | 2 | 3 | 3 | 1 | 3 |
| | | 48 H | 3 | 2 | 1 | 2 | 3 | 3 | 3 | 3 |
| E. coli | 206 | 24 H | 3 | 1 | 1 | 3 | 3 | 3 | 2 | 3 |
| | | 48 H | 3 | 1 | 1 | 3 | 3 | 3 | 3 | 3 |
| S. marcescens | 042 | 24 H | — | — | — | — | — | — | — | — |
| | | 48 H | 1 | 1 | — | 2 | 3 | 1 | — | 3 |
| E. cloacae | 061 | 24 H | 2 | 1 | — | 2 | 2 | 2 | 1 | 2 |
| | | 48 H | 2 | 1 | 1 | 2 | 2 | 2 | 3 | 2 |
| P. vulgaris | 140 | 24 H | — | — | — | — | — | — | — | — |
| | | 48 H | — | — | — | — | — | — | — | — |
| E. faecalis | 117 | 24 H | — | — | — | — | — | — | — | — |
| | | 48 H | — | — | — | — | — | — | — | — |
| E. faecium | 255 | 24 H | 1 | — | — | — | — | — | — | — |
| | | 48 H | 3 | 1 | — | 1 | 3 | — | — | — |
| S. aureus | 008 | 24 H | — | — | — | — | — | — | — | — |
| | | 48 H | — | — | — | — | — | — | — | — |

*intensity of coloration (arbitrary scale based on a visual observation);
— signifies a lack of coloration;
TI signifies time of incubation While X-Gal makes it possible to detect an activity on the *E. faecium* strain, unlike PNB-Gal, for the strains which strongly hydrolyze X-Gal under aerobiosis (*E. coli, E. cloacae*), PNB-Gal makes it possible to detect this β-D-galactosidase activity independently of the atmosphere and more intensely. Specifically, while the intensities are weak or very weak under the conditions of test 3, they are strong under the conditions of test 7.

EXAMPLE 11

Use of 8-chloro-1,2-benzoresorufin-β-D-galactoside (CBR-gal) for Detecting Microorganisms having β-galactosidase Activity in a Solid Medium The CBR-gal substrate is incorporated into a Columbia agar at the following concentrations: 2, 6, 10 and 20 mg/100 ml, and the medium thus prepared is distributed into dishes. Each dish is inoculated with the following organisms: *E. coli* (NCTC, 10418), *K. pneumoniae* (NCTC, 10896), *P. rettgeri* (NCTC, 7475), *E. cloacae* (NCTC, 11936), *S. marcescens* (NCTC, 10211) and *S. typhimurium* (NCTC, 74). IPTG is incorporated into all these media, at a concentration of 3 mg per 100 ml of Columbia agar. All the dishes are incubated at 37° C. overnight.

The strains positive for β-galactosidase activity (*E. coli, K. pneumoniae, E. cloacae* and *S. marcescens*) rapidly hydrolyze the substrate after an overnight incubation, giving a pink coloration which is limited to the bacterial colony. All the concentrations tested make it possible to differentiate these species, but the optimum concentration to obtain a clearly visible pink coloration without any background noise is around 10 mg/100 ml. No inhibition of growth is visible for any of the concentrations tested.

EXAMPLE 12

Use of 8-chloro-1,2-benzoresorufin-β-D-galactoside (CBR-gal) for Detecting Microorganisms having β-galactosidase Activity in a Liquid Medium The CBR-gal substrate is tested in a liquid medium, at various concentrations from 0.5 mg/ml to 0.0078 mg/ml. The liquid reaction medium into which the substrate is incorporated is composed of a phosphate buffer, pH 7.4, containing 0.5% of nutrient broth and 0.5% of NaCl. 30 microliters/ml of IPTG are added to the medium for all the substrate concentrations. The strains tested are *E. coli* (NCTC, 10418), *K. pneumoniae* (NCTC, 10896), *P. rettgeri* (NCTC, 7475), *E. cloacae* (NCTC, 11936), *S. marcescens* (NCTC, 10211) and *S. typhimurium* (NCTC, 74), with an inoculum of 0.5 McFarland.

All the strains having β-galactosidase activity generate a pink coloration over time, as summarized in table V below.

What is claimed is:

1. An enzymatic substrate of general formula (I):

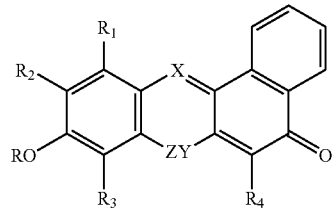

in which
 X represents a nitrogen atom or a carbon atom substituted with a phenyl group, said phenyl group optionally being substituted in the meta or para position,
 Y and Z represent a hydrogen atom when X represents a carbon atom, or Y and Z together represent an ether, thioether or amine bond optionally substituted with an alkyl or aryl group,
 $R_1$ and $R_2$ each represent, independently of one another, H, Cl, F, I or Br, and may be identical or different, or $R_1$ and $R_2$ together represent a fused benzene ring which may or may not be substituted,
 $R_3$ and $R_4$ each represent, independently of one another, H, Cl, F, I or Br and may be identical or different, and
 R represents a group such that the O—R bond can be hydrolyzed by an enzyme, wherein R is selected from the group consisting of an α- or β-sugar-type residue, a phosphate, and a sulfate.

2. The enzymatic substrate as claimed in claim 1, characterized in that the enzyme is selected from the group consisting of osidases, hexosaminidases, esterases, lipases, phosphatases, sulfatases, DNAases, peptidases and proteases.

3. An enzymatic substrate of general formula (II):

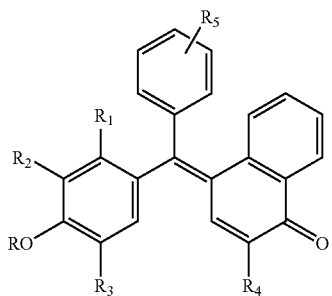

in which,

TABLE V

| | Concentration of CBR-gal substrate | | | | | | |
|---|---|---|---|---|---|---|---|
| Organisms | 0.5 mg/ml | 0.25 mg/ml | 0.125 mg/ml | 0.0625 mg/ml | 0.0313 mg/ml | 0.0156 mg/ml | 0.0078 mg/ml |
| *E. coli* | 2* | 2 | 4 | 4 | 24 | — | — |
| *K. pneumoniae* | 2 | 2 | 4 | 4 | 24 | — | — |
| *P. rettgeri* | — | — | — | — | — | — | — |
| *E. cloacae* | 2 | 2 | 4 | 4 | 24 | — | — |
| *S. marcescens* | 24 | 24 | 24 | 24 | 24 | — | — |
| *S. typhimurium* | — | — | — | — | — | — | — |

*the results are given in hours.
— signifies a lack of coloration, even after 24 hours.

$R_1$ and $R_2$ each represent, independently of one another, H, Cl, F, I or Br, and may be identical or different, or $R_1$ and $R_2$ together represent a fused benzene ring which may or may not be substituted, $R_3$ and $R_4$ each represent, independently of one another, H, Cl, F, I or Br, and may be identical or different, $R_5$ represents H, $NO_2$, $CF_3$, CN, $OCH_3$, F, I, Cl, Br, $SO_3H$ or $CO_2H$ in the meta or para position, and R represents a group such that the O—R bond can be hydrolyzed by an enzyme.

4. The enzymatic substrate as claimed in claim 3, characterized in that
$R_1$ and $R_2$ together represent a fused benzene ring,
$R_3$ and $R_4$ represent a hydrogen atom,
$R_5$ represents a hydrogen,
R represents a residue of the α- or α-sugar type, a sulfate or an acetate.

5. An enzymatic substrate of general formula (III)

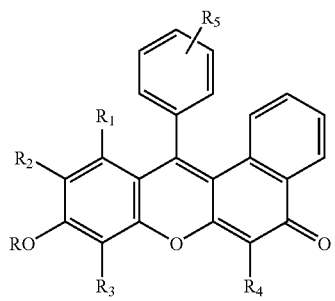

(III)

in which,
$R_1$ and $R_2$ each represent, independently of one another, H, Cl, F, I or Br, and may be identical or different, or $R_1$ and $R_2$ together represent a fused benzene ring which may or may not be substituted, $R_3$ and $R_4$ each represent, independently of one another, H, Cl, F, I or Br, and may be identical or different, $R_5$ represents H, $NO_2$, $CF_3$, CN, $OCH_3$, F, I, Cl, Br, $SO_3H$ or $CO_2H$ in the meta or para position, and R represents a group such that the O—R bond can be hydrolyzed by an enzyme.

6. The enzymatic substrate as claimed in claim 5, characterized in that
$R_1$ and $R_2$ together represent a fused benzene ring,
$R_3$ and $R_4$ represent a hydrogen atom,
$R_5$ represents H,
R represents a residue of the α- or β-sugar type.

7. The enzymatic substrate as claimed in claim 1, of general formula (IVa):

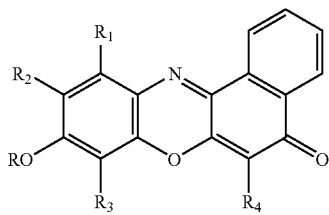

(IVa)

in which,
$R_1$ and $R_2$ each represent, independently of one another, H, Cl, F, I or Br, and may be identical or different, or $R_1$ and $R_2$ together represent a fused benzene ring which may or may not be substituted, $R_3$ and $R_4$ each represent, independently of one another, H, Cl, F, I or Br, and may be identical or different, and R represents a group such that the O—R bond can be hydrolyzed by an enzyme, wherein R is selected from the group consisting of an α- or β-sugar-type residue a phosphate, and a sulfate.

8. The enzymatic substrate as claimed in claim 1, of general formula (IVb):

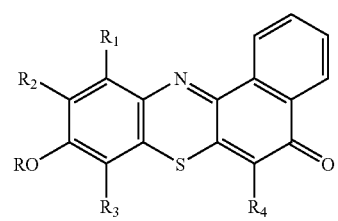

(IVb)

in which,
$R_1$ and $R_2$ each represent, independently of one another, H, Cl, F, or Br, and may be identical or different, or $R_1$ and $R_2$ together represent a fused benzene ring which may or may not be substituted, $R_3$ and $R_4$ each represent, independently of one another, H, Cl, F, I or Br, and may be identical or different, and R represents a group such that the O—R bond can be hydrolyzed by an enzyme, wherein R is selected from the group consisting of an α- or β-sugar-type residue, a phosphate, and a sulfate.

9. An enzymatic substrate of general formula (IVc):

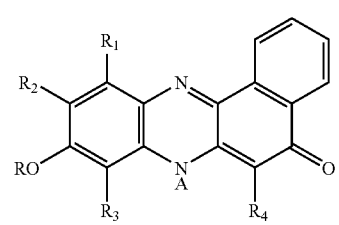

(IVc)

in which,
A represents an aryl or alkyl group,
$R_1$ and $R_2$ each represent, independently of one another, H, Cl, F, I or Br, and may be identical or different, or $R_1$ and $R_2$ together represent a fused benzene ring which may or may not be substituted, $R_3$ and $R_4$ each represent, independently of one another, H, Cl, F, I or Br, and may be identical or different, and R represents a group such that the O—R bond can be hydrolyzed by an enzyme.

10. The enzymatic substrate as claimed in claim 7, characterized in that,
$R_1$ represents H and $R_2$ represents $C_1$,
$R_3$ and $R_4$ represent H, and
R represents a residue of the α- or β-sugar type.

11. The enzymatic substrate as claimed in claim 9, characterized in that,
$R_1$, $R_3$ and $R_4$ represent H,
A represents a phenyl,
R represents a residue of the α- or β-sugar type.

12. A method for synthesizing an enzymatic substrate as claimed in claim 1 comprising:
preparing an intermediate compound, which is of general formula (V):

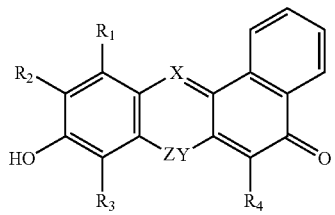

(V)

in which
- X represents a nitrogen atom or a carbon atom substituted with a phenyl group, said phenyl group optionally being substituted in the meta or para position,
- Y and Z represent a hydrogen atom when X represents a carbon atom, or Y and Z together represent an ether, thioether or amine bond optionally substituted with an alkyl or aryl group,
- $R_1$ and $R_2$ each represent, independently of one another, H, Cl, F, I or Br, and may be identical or different, or $R_1$ and $R_2$ together represent a fused benzene ring which may or may not be substituted,
- $R_3$ and $R_4$ each represent, independently of one another, H, Cl, F, I or Br, and may be identical or different and grafting a suitably protected group R onto the hydroxyl.

13. The method as claimed in claim 12, characterized in that the intermediate compound corresponds to the following formula (Va)

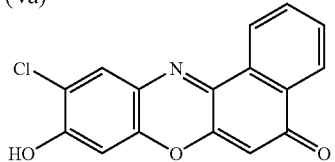

14. The method as claimed in claim 12, characterized in that the intermediate compound corresponds to the following formula (Vb)

(Vb)

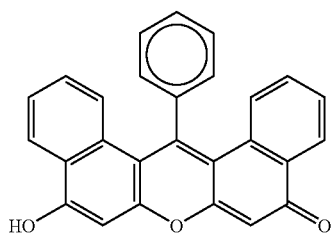

15. The method as claimed in claim 12, characterized in that the intermediate compound corresponds to the following formula (Vc)

(Vc)

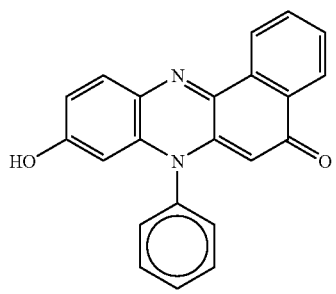

16. A composition for at least one of detecting, identifying or quantifying at least one microorganism, comprising at least one enzymatic substrate and a reaction medium suitable for said at least one microorganism, wherein said at least one enzymatic substrate is of general formula (1):

(I)

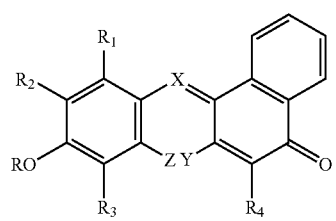

in which
- X represents a nitrogen atom or a carbon atom substituted with a phenyl group, said phenyl group optionally being substituted in the meta or para position,
- Y and Z represent a hydrogen atom when X represents a carbon atom, or Y and Z together represent an ether, thioether or amine bond optionally substituted with an alkyl or aryl group,
- $R_1$ and $R_2$ each represent, independently of one another, H, Cl, F, I or Br, and may be identical or different, or $R_1$ and $R_2$ together represent a fused benzene ring which may or may not be substituted,
- $R_3$ and $R_4$ each represent, independently of one another, H, Cl, F, I or Br and may be identical or different, and
- R represents a group such that the O—R bond can be hydrolyzed by an enzymes wherein R is selected from the group consisting of an α- or β-sugar-type residue, a phosphate and a sulfate.

17. The composition as claimed in claim 16, characterized in that the reaction medium is solid, semi-solid or liquid.

18. The composition as claimed in claim 16, characterized in that the concentration of the enzymatic substrate in the reaction medium is between 0.02 and 1 g/l.

19. A diagnostic kit comprising a composition as claimed in claim 16 and a container for the reaction medium.

20. A method for at least one of detecting, identifying or quantifying at least one microorganism in a specimen, comprising:

contacting the microorganism originating from the specimen with a reaction medium containing an enzymatic substrate so as to obtain an inoculating medium, and detecting the colored or fluorescent product formed by the hydrolysis of said enzymatic substrate, wherein said enzymatic substrate is of general formula (I):

(I)

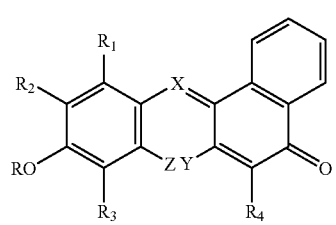

in which
- X represents a nitrogen atom or a carbon atom substituted with a phenyl group, said phenyl group optionally being substituted in the meta or para position, Y and Z represent a hydrogen atom when X represents a carbon atom, or Y and Z together represent an ether, thioether or amine bond optionally substituted with an alkyl or aryl group, $R_1$ and $R_2$ each represent, independently of one another, H, Cl, F, I or Br, and may be identical or different, or $R_1$ and $R_2$ together represent a fused benzene ring which may or may not be substituted, $R_3$ and $R_4$ each represent, independently of one another, H, Cl, F, I or Br and may be identical or different, and R represents a group such that the O—R bond can be hydrolyzed by an enzyme.

21. The method as claimed in claim 20, characterized in that the inoculated reaction medium is incubated in a controlled atmosphere.

22. The enzymatic substrate as claimed in claim 2, wherein the osidase is selected from the group consisting of β-glucuronidase, β-galactosidase, β-glucosidase, 6-phosphogalactohydrolase, α-galactosidase, α-amylase, and α-glucosidase.

23. The enzymatic substrate as claimed in claim 2, wherein the hexosaminidase is N-acetyl-β-glucosaminidase or N-acetyl-β-galactosaminidase.

24. The enzymatic substrate as claimed in claim 1, wherein the α- or β-sugar type residue is β-D-glucose, β-D-galactose or β-D-glucuronate.

25. The enzymatic substrate as claimed in claim 4, wherein the α- or β-sugar type residue is β-D-glucose or β-D-galactose.

26. The enzymatic substrate as claimed in claim 6, wherein the α- or β-sugar type residue is β-D-glucose or β-D-galactose.

27. The enzymatic substrate as claimed in claim 7, wherein $R_1$ represents H and $R_2$ represents Cl.

28. The enzymatic substrate as claimed in claim 7, wherein $R_3$ and $R_4$ represent H.

29. The enzymatic substrate as claimed in claim 7, wherein R is an α- or β-sugar type residue.

30. The enzymatic substrate as claimed in claim 8, wherein $R_1$ represents H and $R_2$ represents Cl.

31. The enzymatic substrate as claimed in claim 8, wherein $R_3$ and $R_4$ represent H.

32. The enzymatic substrate as claimed in claim 8, wherein R is an α- or β-sugar type residue.

33. The enzymatic substrate as claimed in claim 9, wherein $R_1$ represents H and $R_2$ represents Cl.

34. The enzymatic substrate as claimed in claim 9, wherein $R_3$ and $R_4$ represent H.

35. The enzymatic substrate as claimed in claim 9, wherein R is an α- or β-sugar type residue.

36. The enzymatic substrate as claimed in claim 10, wherein α- or β-sugar type residue is β-D-glucose or β-D-galactose.

37. The enzymatic substrate as claimed in claim 11, wherein R is an α- or β-sugar type residue.

38. The method as claimed in claim 21, wherein the controlled atmosphere is at least one of aerobic, anaerobic, microaerophilic and under an atmosphere of $CO_2$.

39. The method as claimed in claim 21, wherein the controlled atmosphere is aerobic, microaerophilic and under $CO_2$ conditions.

40. A method of detecting an analyte selected from the group consisting of an antibody, an antigen and a nucleic acid, said method comprising:

binding an enzyme to said analyte, if present, to form enzyme bound to said analyte if analyte is present;

bringing any said enzyme bound to said analyte into contact with an enzymatic substrate as claimed in claim 1, wherein said enzymatic substrate is hydrolyzed by any said enzyme bound to said analyte to form a hydrolysis product of said enzymatic substrate if said enzyme bound to said analyte is present; and detecting the hydrolysis product.

41. The method as claimed in claim 40, wherein the technique using enzymatic activity is ELISA.

42. The method as claimed in claim 40, wherein the analyte is a gene of β-galactosidase type.

43. A composition according to claim 16, comprising at least two said enzymatic substrates, wherein the enzymatic hydrolysis of the enzymatic substrates produces different colored and/or fluorescent products.

44. A composition according to claim 16, further comprising another enzymatic substrate, which is different from said at least one enzymatic substrate, wherein the enzymatic hydrolysis of the another enzymatic substrate produces a colored or fluorescent product that is different from the colored or fluorescent product released by the enzymatic hydrolysis of said at least one enzymatic substrate.

45. The enzymatic substrate according to claim 29, wherein the α- or β-sugar type residue is selected from the group consisting of β-D-glucose and β-D-galactose.

46. The enzymatic substrate as claimed in claim 32, wherein the α- or β-sugar type residue is selected from the group consisting of β-D-glucose and β-D-galactose.

47. The enzymatic substrate as claimed in claim 35, wherein α- or β-sugar type residue is selected from the group consisting of β-D-glucose and β-D-galactose.

48. The composition as claimed in claim 18, wherein the concentration of the enzymatic substrate in the reaction medium is between 0.03 to 0.30 g/l.

49. The composition as claimed in claim 18, wherein the concentration of the enzymatic substrate in the reaction medium is between 0.04 and 0.10 g/l.

50. Agent for at least one of detecting, identifying or quantifying at least one microorganism, comprising at least one enzymatic substrate and a reaction medium suitable for said at least one microorganism, wherein said at least one enzymatic substrate is of general formula (I):

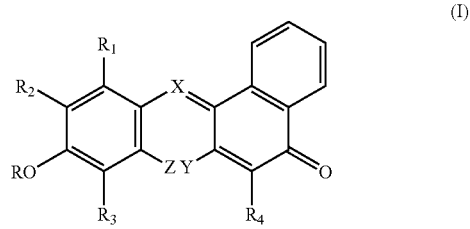

in which

X represents a nitrogen atom or a carbon atom substituted with a phenyl group, said phenyl group optionally being substituted in the meta or para position, Y and Z represent a hydrogen atom when X represents a carbon atom, or Y and Z together represent an ether, thioether or amine bond optionally substituted with an alkyl or aryl group, $R_1$ and $R_2$ each represent, independently of one another, H, Cl, F, I or Br, and may be identical or different, or $R_1$ and $R_2$ together represent a fused benzene ring which may or may not be substituted, $R_3$ and $R_4$ each represent, independently of one another, H, Cl, F, I or Br and may be identical or different, and R represents a group such that the O—R bond can be hydrolyzed by an enzyme, wherein R is selected from the group consisting of an α- or β-sugar-type residue, a phosphate and a sulfate.

* * * * *